United States Patent [19]

Davies et al.

[11] 4,175,057
[45] Nov. 20, 1979

[54] ZEOLITE COMPOSITION

[75] Inventors: Evan E. Davies, Woking; Alexander J. Kolombos, Thames Ditton, both of England

[73] Assignee: The British Petroleum Company Limited, London, England

[21] Appl. No.: 856,668

[22] Filed: Dec. 2, 1977

[30] Foreign Application Priority Data

Dec. 20, 1976 [GB] United Kingdom ............... 53012/76

[51] Int. Cl.$^2$ ............................................ B01J 29/06
[52] U.S. Cl. ................................ 252/455 Z; 423/112
[58] Field of Search .................. 252/455 Z; 423/118, 423/328, 112

[56] References Cited

U.S. PATENT DOCUMENTS

| 3,010,789 | 11/1961 | Milton | 423/328 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 4,025,571 | 5/1977 | Lago | 423/328 X |
| 4,056,575 | 11/1977 | Gregory et al. | 260/673.5 |

*Primary Examiner*—Carl Dees
*Attorney, Agent, or Firm*—Brooks, Haidt, Haffner & Delahunty

[57] ABSTRACT

This case relates to a process for producing aromatics by contacting a $C_3$–$C_8$ hydrocarbon with a gallium catalyst supported on an aluminosilicate in which the ratio of silica to alumina is between 20:1 and 70:1.

5 Claims, 1 Drawing Figure

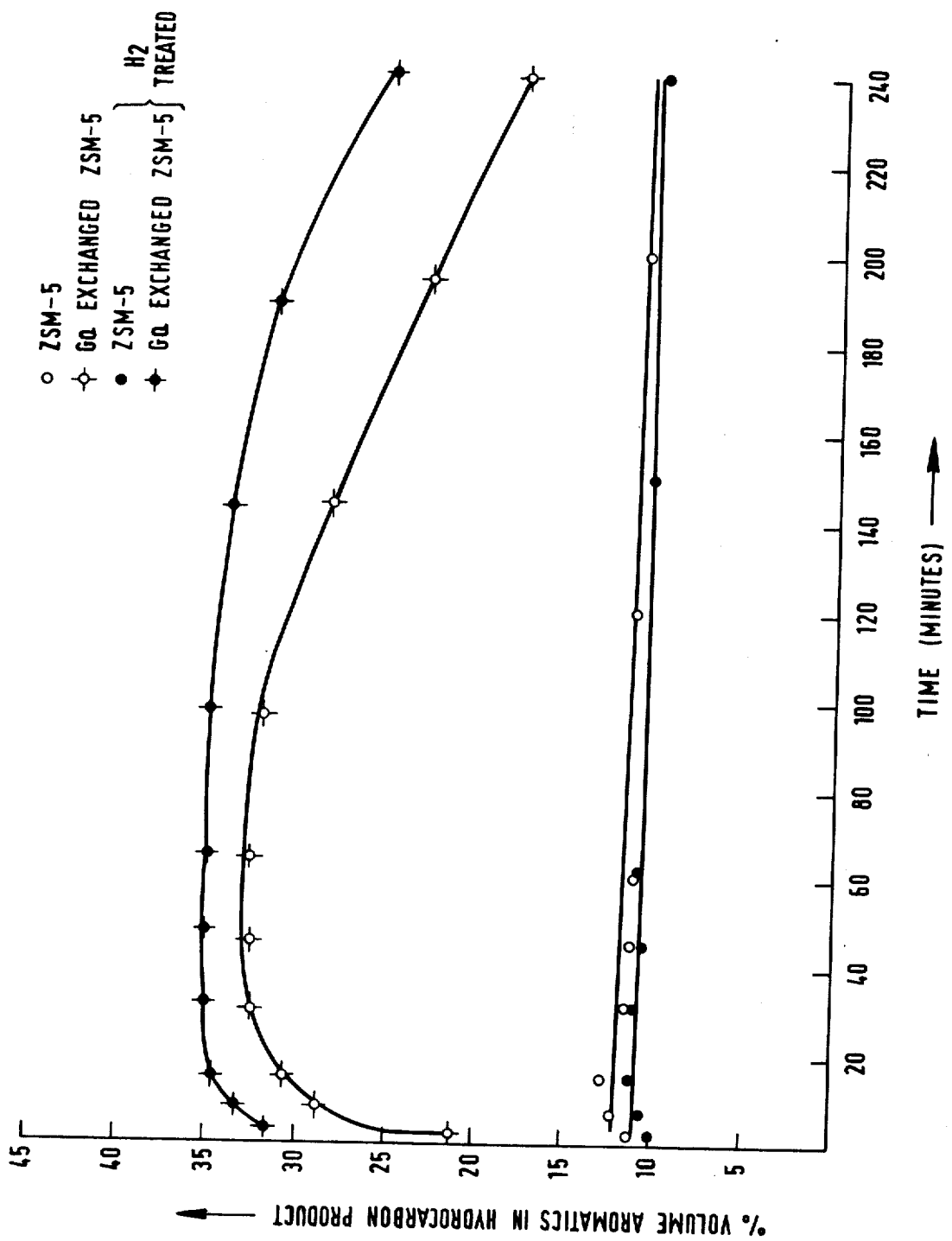

ZEOLITE COMPOSITION

The present invention relates to a zeolite composition and to the use thereof for producing aromatic hydrocarbons from aliphatic hydrocarbon feedstock.

Conventional aluminosilicates including zeolites and alumina have been used in the past in the preparation of catalysts for the production of aromatic hydrocarbons from open chain hydrocarbons. The open chain hydrocarbon is passed over the catalyst at an elevated temperature in the liquid or vapour phase. Zeolites of various types, particularly those containing a high silica to alumina ratio, have been suggested for the preparation of such catalysts. Examples of such zeolites are mordenite and the ZSM varieties. Such zeolites have been known to contain gallium in the form of its oxide which is substituted either partially or wholly for the aluminium oxide present therein. These zeolites however contain gallium as part of the crystal structure of the zeolite and the gallium is non-ionic. However, the yields of aromatic hydrocarbons from such open chain hydrocarbons have been unsatisfactory when using catalysts prepared from such zeolites.

It has now been found that, by using catalysts which contain gallium and which are prepared from specific types of aluminosilicates, improved yields of aromatic hydrocarbons may be obtained.

It has further been found that if, instead of preparing the zeolite with gallium forming part of the crystal structure, gallium is either exchanged for one of the cations or protons, or impregnated into the zeolitic cavities, surprisingly high catalytic activity is obtained especially in hydrocarbon conversion processes.

Accordingly, the present invention is a process for producing aromatic hydrocarbons comprising bringing into contact at an elevated temperature a $C_3$–$C_{12}$ hydrocarbon feedstock as hereinafter defined and a catalyst composition comprising an aluminosilicate having gallium deposited thereon and/or an aluminosilicate in which cations have been exchanged with gallium ions, said aluminosilicate containing silica to alumina in a molar ratio of between 20:1 and 70:1.

According to a further embodiment the present invention also comprises a zeolite composition comprising an aluminosilicate having a molar ratio of silica to alumina of between 20:1 and 70:1 in which cations as hereinafter defined have been exchanged with gallium ions.

By $C_3$–$C_{12}$ feedstock is meant here and throughout the specification a feedstock containing a single hydrocarbon component or mixtures of saturated and/or unsaturated $C_3$–$C_{12}$ hydrocarbons. The feedstock is suitably a $C_3$–$C_8$ hydrocarbon feedstock. $C_4$ feeds containing isobutane and/or isobutene in the feedstock are particularly useful.

The gallium in the catalyst composition may be present as gallium oxide and/or as gallium ions if cations in the aluminosilicate support have been exchanged with gallium ions. In the case where the cations in the aluminosilicate have been exchanged for gallium ions, the gallium ion is suitably provided as an aqueous solutions of gallium salts such as for instance gallium nitrate, gallium chloride or gallium sulphate. Such catalysts may be produced by conventional ion exchange techniques and the catalysts so produced are subsequently dried. For example an aqueous solution of a gallium compound such as gallium nitrate may be placed in contact with the aluminosilicate at ambient or elevated temperature, eg. by refluxing. The exchanged aluminosilicate is then separated by decantation followed by filtration, washed several times with deionised water and finally dried. Before addition to the aqueous solution of the gallium compound, the aluminosilicate may be acid treated.

The aluminosilicates in which such an exchange with gallium ions may be carried out may be selected from zeolite-$\beta$ and zeolites of the general formula $M_{2/n}O \cdot W_2O_3 \cdot yYO_2 zH_2O$ wherein M is a cation which is a positively charged ion selected from a metal ion, an organic ion and a proton of valence n, W is either aluminium, gallium or a mixture of both and Y is either silicon or germanium, y is an integer between 20 and 70 and z is from 0 to 40. The metal ion is preferably an alkali metal or alkaline earth metal ion, preferably sodium or potassium ions. The organic ions may suitably be represented by the formulae $R^1R^2R^3R^4N^+$ or by an ion derived from the diamine $R^1R^2N\,(CH_2)_x NR^3R^4$ or pyrrolidine where $R^1R^2R^3$ and $R^4$ may be H, $CH_3$, $C_2H_5$, $C_3H_7$ or $C_4H_9$ and x equals 2, 3, 4, 5 or 6. The ZSM variety of zeolites, for example ZSM-5, ZSM-8, ZSM-11, ZSM-12 and ZSM-35 are particularly preferred and these are extensively described in a number of publications including U.S. Pat. No. 3,970,544 (Mobil).

The process of the present invention may also be carried out using catalysts in which gallium is only impregnated on the surface of the aluminosilicate or is incorporated in the intracrystalline zeolite cavities as a gallium compound which gives rise to gallium oxide during activation of the catalyst prior to contact with the hydrocarbon feedstock. An example of a suitable gallium compound is gallium nitrate. Conventional impregnation techniques may be used to produce these catalysts.

The impregnation may be achieved by preparing a solution, suitably an aqueous solution, of a gallium compound such as for example gallium nitrate and adding a conventional aluminosilicate to this aqueous solution with thorough stirring to form a paste. The paste is subsequently dried at an elevated temperature in vacuum.

Where the catalyst composition is prepared by using a compound of gallium which ionises in aqueous solution for example gallium nitrate it is inevitable that some of the gallium ions will be exchanged with the cations in the aluminosilicate even if the preparation was directed to impregnation of the aluminosilicate.

Whichever method of catalyst preparation is used, the amount of galium present in the catalyst compositions may vary for instance between 0.1 and 10%, preferably between 0.5 and 7% by weight of the total aluminosilicate in the catalyst composition.

The catalyst composition is suitably activated prior to contact with the hydrocarbon feedstock. The activation may be carried out by heating the catalyst at a temperature of between 400° and 650° C., preferably between 500° and 600° C. Activation may be carried out in an atmosphere of hydrogen, air or a gas inert under the reaction conditions such as nitrogen, but most preferably in an atmosphere of hydrogen. The activation may be carried out in the reactor tube itself prior to the reaction. The catalyst composition is suitably used as a fixed bed.

The hydrocarbon feedstock as hereinbefore described is thereafter passed preferably in the vapour phase over the catalyst composition at a temperature between 450° and 700° C. preferably between 500° and 600° in an inert atmosphere. The inert atmosphere may be provided by a gas inert under the reaction conditions such as nitrogen. The products of the reaction are then identified and isolated.

The invention is further illustrated with reference to the following Examples.

EXAMPLE 1

4.88 g of gallium nitrate was dissolved in 20 ml of distilled water. 13 g of zeolite-$\beta$ was added and thoroughly stirred to a paste. The catalyst composition was dried in a vacuum oven for 60 hours.

15 mls of the catalyst composition (6% wt gallium) were loaded into a reactor and heated for 18 hours at 550° C. in a stream of air. The reactor was cooled to 450° and isobutene introduced at atmospheric pressure and a contact time of 7.1 seconds. Analysis of the product stream showed that 86.1% wt of the isobutene had been converted. The major products of the reaction were: $C_1$-$C_3$ hydrocarbons 17.2% wt; other $C_4$ hydrocarbons 33.9% wt; aromatics 24.9% wt.

EXAMPLE 2

0.88 g of gallium nitrate was dissolved in 20 ml of distilled water. 13 g of ZSM-12 was added and thoroughly stirred into a paste. The catalyst composition was dried in a vacuum oven for 16 hours.

15 mls of the catalyst composition (1% wt gallium) was loaded into a reactor and heated at 550° C. for 18 hours in a stream of air. The reactor was cooled to 500° C. and isobutene introduced at atmospheric pressure and a contact time of 6.94 seconds. Analysis of the product stream showed that 97.1% of the isobutene had been converted. The major products of the reaction were: $C_1$-$C_3$ hydrocarbons 19.7% wt; other $C_4$ hydrocarbons 21.3% wt; aromatics 39.4% wt.

EXAMPLE 3

15 mls of the gallium (1% wt) impregnated ZSM-12 prepared as described in Example 2 was heated in a reactor at 550° C. for 18 hours in a flow of air. Isobutene was then introduced at 550° C., atmospheric pressure and a contact time of 6.3 seconds. Analysis of the product stream showed that 66.5% wt of the isobutene had been converted. The major products of the reaction were: $C_1$-$C_3$ hydrocarbons 22.5% wt; $C_4$ hydrocarbons 18.6% wt; aromatics 35.9% wt.

EXAMPLE 4

4.88 g of gallium nitrate were dissolved in 20 mls of water. 13 g of zeolite ZSM-8 were added and thoroughly stirred to a paste which was dried in a vacuum oven for 60 hours.

15 mls of the catalyst composition (6% wt gallium) were loaded into a reactor and heated at 550° C. for 2 hours in an air stream. The temperature was then raised to 650° C. and isobutene introduced at atmospheric pressure and a contact time of 5.7 seconds. 84.7% wt of the isobutene was converted. The major products of the reactor were: $C_1$-$C_3$ hydrocarbons 22.5% wt; $C_4$ hydrocarbons 18.6% wt; aromatics 35.9% wt.

EXAMPLE 5

4.88 g of gallium were dissolved in 20 mls of water. 3.51 g of Ludox silica sol (40% wt gallium) 11.7 g of zeolite ZSM-5 were added and the mixture stirred well and dried overnight in the vacuum oven.

15 mls of the catalyst composition (6% wt gallium) were loaded into a reactor and heated at 550° C. for 6 hours in a stream of air. Isobutene was then introduced at 550° C., atmospheric pressure and a contact time of 6.17 seconds. 99.6% wt of the isobutene was converted. The major products of the reactions were: $C_1$-$C_3$ hydrocarbons 38.8% wt; other $C_4$ hydrocarbons 3.5% wt; aromatics 47.3% wt.

EXAMPLE 6

15 mls of the gallium (6% wt) impregnated ZSM-5 prepared as described in Example 5 was heated for 2 hours at 550° C. in a stream of air. Isobutane was then introduced at 550° C., atmospheric pressure and with a contact time of 5.67 seconds. 98.8% wt of the isobutane was converted. The major products of the reaction were: $C_1$-$C_3$ hydrocarbons 45.3% wt; other $C_4$ hydrocarbons 2.5% wt; aromatics 44.9% wt.

EXAMPLE 7

8.2 g of gallium nitrate were dissolved in 100 mls of water and ammonia solution added until the pH was 2.5. 22 g of ZSM-5 zeolite was then added to the gallium solution and the mixture heated under reflux for 24 hours and then filtered. The resulting slurry was then allowed to stand in distilled water for 24 hours. The mixture was then filtered again and dried in a vacuum oven for 15 hours at 150° C.

15 mls of this gallium (1.69%) exchanged ZSM-5 catalyst composition was loaded into a reactor and heated for 18 hours at 550° C. in a stream of air. Isobutane was then introduced at 550° C., atmospheric pressure and a contact time of 5.86 seconds. 93.8% wt of the isobutane was converted. The major products of the reaction were: $C_1$14 $C_3$ hydrocarbons 37.1% wt; other $C_4$ hydrocarbons 2.6% wt; aromatics 44.5% wt. The figure (accompanying the specification) shows the variation of % volume of aromatics in the hydrocarbon product with time for the gallium exchanged ZSM-5 catalyst composition and for ZSM-5 alone. The beneficial effect of the gallium exchange can clearly be seen.

EXAMPLE 8

15 mls of the gallium (1.69% wt) exchanged zeolite prepared as described in Example 7 were loaded into a reactor and heated for 18 hours at 550° C. in a stream of air. The catalyst composition was then heated for a further 3 hours in a stream of hydrogen. Isobutane was then introduced at 550° C. atmospheric pressure and a contact time of 5.86 seconds. 85.7% wt of the isobutane was converted. The major products of the reaction were: $C_1$-$C_3$ hydrocarbons 28.5% wt; other $C_4$ hydrocarbons 0.3% wt; aromatics 47.4% wt. the figure accompanying the specification shows the variation of % volume of aromatics in hydrocarbon product with time for the hydrogen-preheated gallium exchanged catalyst and for the hydrogen pretreated ZSM-5. The Figure shows the beneficial effect of the hydrogen pretreatment on the gallium exchanged ZSM-5. Gallium exchange increases aromatics yield and catalyst life. Comparison of Examples 8 and 7 also shows that hydrogen pretreatment reduces the yield of undesirable $C_1$-$C_3$ hydrocarbons.

EXAMPLE 9

9 grams of gallium metal were dissolved in 150 mls concentrated nitric acid. 90 mls of this solution were then diluted to 200 mls by addition of an ammonia solution and a further 200 mls of deionised water were added giving a resulting solution with a pH of 2. 130 grams of ZSM-8 were then refluxed with this solution for 24 hours. After refluxing the remaining solution was decanted and the solid extensively washed with deionised water. 110 grams of the gallium exchanged ZSM-8 were then slurried with a silica sol containing 16.5 grams of silica. The resulting slurry was dried at 45° C. overnight in a vacuum oven and then granulated to 8–30 mesh. The resulting catalyst contained 1.7% wt gallium measured on a stable weight at 550° C. basis. This catalyst was reduced for 2 hours at 550° C. in hydrogen prior to use.

A light catalytically cracked spirit (IBP 26° C. FPB 136.5° C.) having a Bromine No. of 114.7 and a Research Octane Number (clear) of 93.4 was processed over 58 mls of the catalyst prepared as described above at an average bed temperature of 481° C. and an LHSV of 2. The resulting product had a Bromine No. of 33 and a Research Octane Number (clear) of 96.1. This shows that a substantial fraction of the olefins present in the light catalytically cracked spirit had been converted to aromatics.

We claim:

1. A zeolite composition comprising an aluminosilicate having a molar ratio of silica to alumina between about 20:1 and 70:1 in which cations have been exchanged with gallium ions or on which a gallium compound has been deposited.

2. A zeolite composition as defined in claim 1 wherein said gallium compound is a compound which gives rise to gallium oxide on activation.

3. A zeolite composition according to claim 1 wherein the aluminosilicate is selected from zeolite-$\beta$ and a zeolite of the general formula:

$$M_{2/n}O.W_2O_3.yYO_2.zH_2O$$

wherein M is a cation which is a positively charged ion selected from a metal ion, an organic ion and a proton of valence n, W is aluminium, gallium or mixtures thereof, Y is silicon or germanium, y is an integer between 20 and 70 and z is from 0 to 40.

4. A zeolite composition according to claim 3 wherein the aluminosilicate is selected from ZSM-5, ZSM-8, ZSM-11, ZSM-12 and ZSM-35.

5. A zeolite composition comprising an aluminosilicate having a molar ratio of silica to alumina between 20:1 and 70:1 in which cations have been exchanged with gallium ions.